(12) United States Patent
Shaw et al.

(10) Patent No.: US 11,607,504 B2
(45) Date of Patent: Mar. 21, 2023

(54) SYRINGE EXCHANGE DEVICE

(71) Applicants: Retractable Technologies, Inc., Little Elm, TX (US); Thomas J. Shaw, Frisco, TX (US)

(72) Inventors: Thomas J. Shaw, Frisco, TX (US); Kathryn Duesman, Pilot Point, TX (US); Mark Small, Heavener, OK (US); Ni Zhu, Allen, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 679 days.

(21) Appl. No.: 16/569,373

(22) Filed: Sep. 12, 2019

(65) Prior Publication Data
US 2020/0086063 A1     Mar. 19, 2020

Related U.S. Application Data

(60) Provisional application No. 62/730,817, filed on Sep. 13, 2018.

(51) Int. Cl.
| | |
|---|---|
| *A61M 5/32* | (2006.01) |
| *A61M 5/315* | (2006.01) |
| *A61B 50/30* | (2016.01) |
| *A61B 50/36* | (2016.01) |
| *G07F 7/06* | (2006.01) |
| *A47B 46/00* | (2006.01) |

(52) U.S. Cl.
CPC .......... *A61M 5/3278* (2013.01); *A47B 46/00* (2013.01); *A61B 50/3001* (2016.02); *A61B 50/362* (2016.02); *A61M 5/31566* (2013.01); *G07F 7/0609* (2013.01)

(58) Field of Classification Search
CPC ... A61B 50/3001; A61B 50/362; A47B 46/00; G07F 7/0609
USPC .......................................................... 206/366
See application file for complete search history.

(56) References Cited

U.S. PATENT DOCUMENTS

| | | | |
|---|---|---|---|
| 5,277,312 A | 1/1994 | Vumbaca | |
| 5,465,841 A * | 11/1995 | Wilson ................... | A61B 50/36 220/909 |
| 5,740,909 A * | 4/1998 | Nazare ................. | A61B 50/362 206/366 |
| 7,513,363 B2 * | 4/2009 | Brown ................ | A61M 5/3205 312/211 |
| 9,867,951 B2 | 1/2018 | Woehr | |
| 2003/0132129 A1 * | 7/2003 | Erickson ............. | A61M 5/3205 206/366 |
| 2004/0144669 A1 | 7/2004 | Kiehne | |
| 2006/0243619 A1 * | 11/2006 | Brown ................ | A61M 5/3205 206/366 |
| 2006/0243635 A1 * | 11/2006 | Sullivan ............. | A61B 17/3217 206/571 |
| 2008/0314921 A1 | 12/2008 | Geissler | |
| 2009/0120820 A1 * | 5/2009 | Iske ..................... | A61B 50/362 414/808 |

(Continued)

*Primary Examiner* — Jacob K Ackun
(74) *Attorney, Agent, or Firm* — Monty L Ross PLLC; Monty Ross

(57) ABSTRACT

A device configured to receive and safely store a plurality of used needle-containing medical apparatus such as syringes, IV catheter introducers, bodily fluid collection devices and blood collection tube holders and to dispense a sterile medical apparatus having the same or a similar shape, size and configuration as that deposited into the device.

11 Claims, 6 Drawing Sheets

(56) References Cited

U.S. PATENT DOCUMENTS

| | | | |
|---|---|---|---|
| 2009/0230008 A1* | 9/2009 | Miller | A61M 5/3205 604/110 |
| 2009/0255839 A1* | 10/2009 | Erickson | A61M 5/002 206/366 |
| 2010/0084406 A1 | 4/2010 | Erickson et al. | |
| 2011/0011881 A1* | 1/2011 | Sansoucy | A61B 50/3001 221/102 |
| 2011/0060292 A1 | 3/2011 | Schraga | |
| 2015/0034517 A1* | 2/2015 | Erickson | A61M 5/002 206/366 |

* cited by examiner

SYRINGE EXCHANGE DEVICE

BACKGROUND OF THE INVENTION

1. Field of the Invention

This invention relates to medical apparatus comprising a needle used to inject or withdraw bodily fluids or medicines and, more particularly, to a device useful for safely collecting and storing such medical apparatus following use and for subsequently dispensing a new, unused medical apparatus for each used medical apparatus that is safely recovered. Examples of medical apparatus suitable for use with such a device include without limitation syringes, intravenous catheter insertion devices, bodily fluid collection devices, blood collection tube holders and the like.

2. Description of Related Art

A common cause of pathogenic contamination and the associated spread of blood-borne diseases is the reuse of non-sterile syringes and other similar needle-containing medical devices, particularly when such devices are reused by single or multiple individuals. Some such syringes are reused in the illegal administration of drugs but others are reused legally as a cost-saving measure by patients needing periodic injections for the treatment of diseases such as diabetes. Another cause of the spread of blood-borne diseases is accidental or inadvertent needle sticks that sometimes result from a failure of healthcare workers to safely and properly dispose of medical apparatus having contaminated or non-sterile needles, and no matter whether the used needles are covered or uncovered by a needle cap. Although various types of "sharps" containers have previously been disclosed that are designed for and intended for use in safely collecting and storing medical apparatus with exposed or contaminated needles and for preventing the reuse of such medical apparatus or needles pending final disposal or destruction, they are oftentimes not used correctly or at all.

A device is needed that will dispense a new needle-containing medical apparatus only after a previously used medical apparatus having the same or a similar shape, size and configuration is deposited into a secure receptacle pending final disposal. Such a device is not believed to be available currently but is disclosed below.

SUMMARY OF THE INVENTION

Apparatus is now disclosed that is configured to receive and safely store a plurality of used needle-containing medical apparatus such as syringes, 1V catheter introducers, bodily fluid collection devices and blood collection tube holders and to dispense a medical apparatus having the same or a similar shape, size and configuration as that deposited into the device. Upon being deposited into the device by a user, the used medical apparatus is collected with other such medical apparatus inside a secure receptacle pending final disposal. Only after the used medical apparatus has been deposited and secured will the subject device dispense another new and sterile medical apparatus of the same variety to the user. This procedure can be initiated using a touch-screen, keyboard, RFID chip or tag, or any other similarly effective, commercially available technology to assure that the user is authorized to operate the device.

In one embodiment of the invention, the device is installed in a single cabinet comprising a reading/sensing mechanism (also referred to herein as a "keyway") configured to identify, receive and move a used needle-containing medical apparatus into a secure storage receptacle, an access door permitting access to the secure storage receptacle for subsequent collection of the used and/or contaminated medical apparatus by service personnel, a lockable storage and dispensing compartment for providing an inventory of new, sterile medical apparatus with the same or similar configuration and utility as those being deposited into the device for collection and disposal, and a control mechanism with a cooperatively configured apparatus dispensing chute that will dispense one clean and sterile needle-containing medical apparatus for each used or contaminated medical apparatus that is deposited into the device.

In one embodiment of the invention, the reading/receiving/sensing mechanism of the subject device comprises a template configured to receive only such medical apparatus as is intended for use with the subject device. In one embodiment of the invention, the template is made using a plurality of differently configured "latches" that are shaped and positioned to function similarly to the tumblers inside a lock. When constructed in this manner, only those medical apparatus intended for use with the device will be able to pass into the secure storage receptacle and thereby clear the reading/receiving/sensing mechanism in the manner necessary to permit dispensing of a new, sterile medical apparatus. It will be appreciated by those of skill in the art upon reading this disclosure that other parameters or criteria such as weight, opacity, or other electronically recognizable indicia can likewise be used to confirm or authenticate and approve a particular apparatus for receipt and deposit into the device.

BRIEF DESCRIPTION OF THE DRAWINGS

The invention is further described and explained in relation to the following drawings wherein.

DESCRIPTION OF PREFERRED EMBODIMENT

Figure 1:
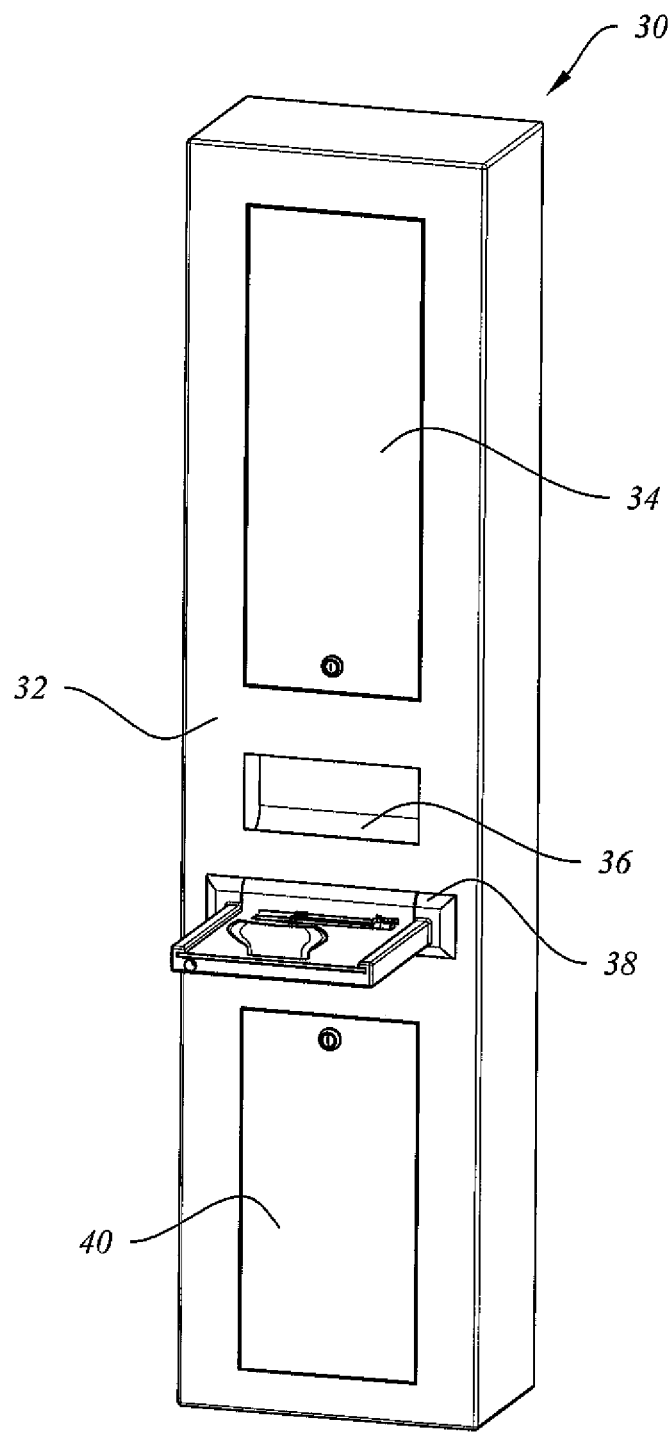
FIG. 1 is a front perspective view of an embodiment of the invention.

The full contents of the specification and drawings of U.S. Provisional Application No. 62/730,817, filed Sep. 13, 2018, are incorporated by reference into this non-provisional application. In one embodiment of the invention as disclosed in FIGS. 1-6, device 30 is installed in a single cabinet 32 comprising a reading/receiving/sensing mechanism 38 (also referred to herein as a "keyway") configured to identify, receive and move a used needle-containing medical apparatus into a secure storage receptacle behind an access door 40 permitting access to the secure storage receptacle for subsequent collection of the used and/or contaminated medical apparatus by service personnel, a lockable storage and dispensing compartment behind new product loading door 34 for providing an inventory of new, sterile medical apparatus with the same or similar configuration and utility as those being deposited into the device for collection and disposal, and a control mechanism with a cooperatively configured apparatus dispensing chute 36 that will dispense one clean and sterile needle-containing medical apparatus for each used or contaminated medical apparatus that is deposited into cabinet 32. In one embodiment of the invention, the reading/receiving/sensing mechanism 38 of the subject device comprises a template 48 configured to receive only such medical apparatus as is intended for use with device 30. In one embodiment of the invention, template 48 is made using a plurality of differently configured "latches" 56 that are shaped and positioned to function similarly to the tumblers inside a lock. When constructed in this manner, only those medical apparatus intended for use with the subject invention will be able to pass into the secure storage receptacle behind access door 40 inside cabinet 32 and thereby clear the reading/receiving/sensing mechanism 38 in the manner necessary to permit dispensing of a new, sterile medical, apparatus.

Referring to FIG. 1, medical apparatus exchange device 30 of the invention comprises one embodiment suitable for use with needle-containing syringes a cabinet 32 enclosed on all sides and having lockable new product loading door 34, syringe dispensing chute 36, syringe reading/receiving/sensing mechanism 38 and lockable access door 40 providing controlled entry into a secure storage receptacle for used syringes.

Figure 2:
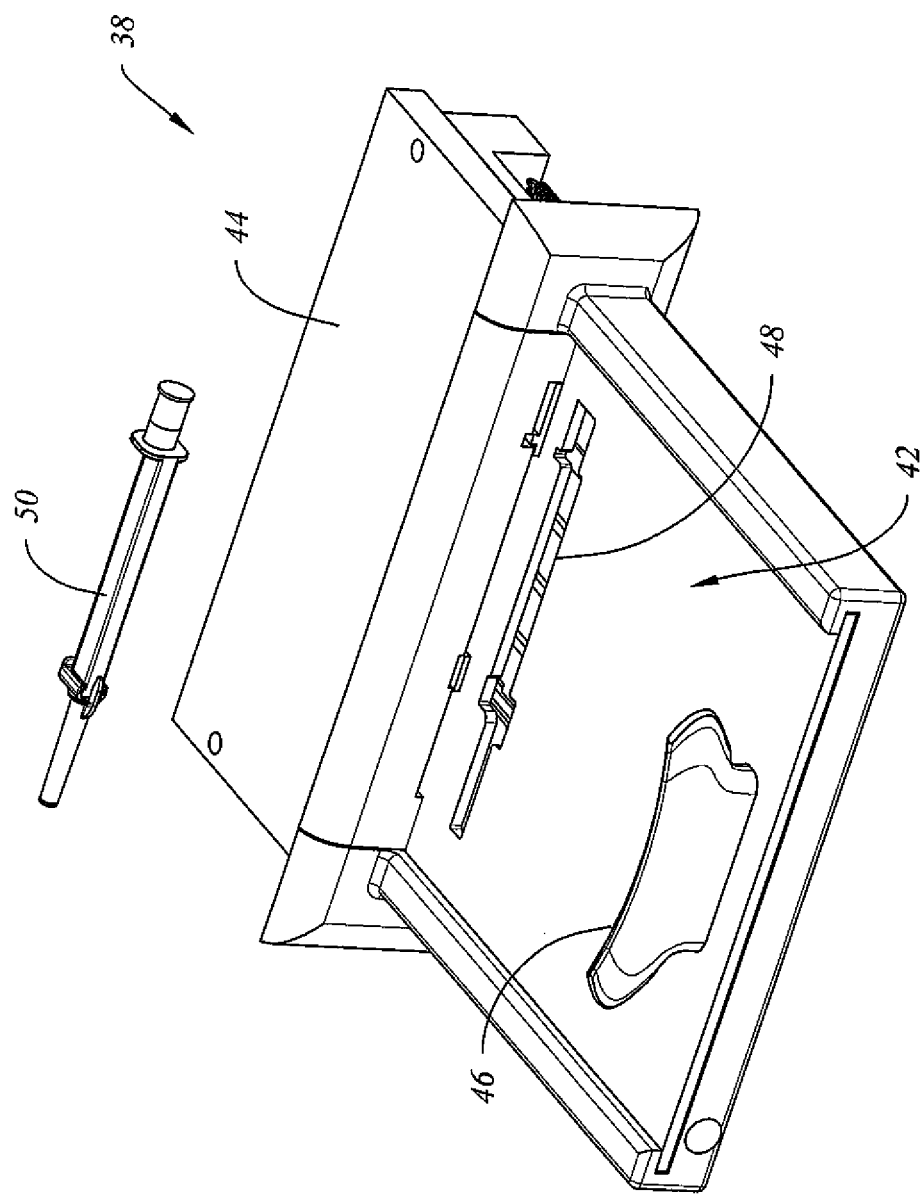
FIG. 2 is a front perspective view of a reading/receiving/sensing mechanism suitable for use in the embodiment of FIG. 1 shown in juxtaposition to a needle-containing syringe prior to depositing the syringe into the template of the drawer or carriage into which the syringe is insertable in exchange for a new, clean and sterile apparatus.
Figure 3:
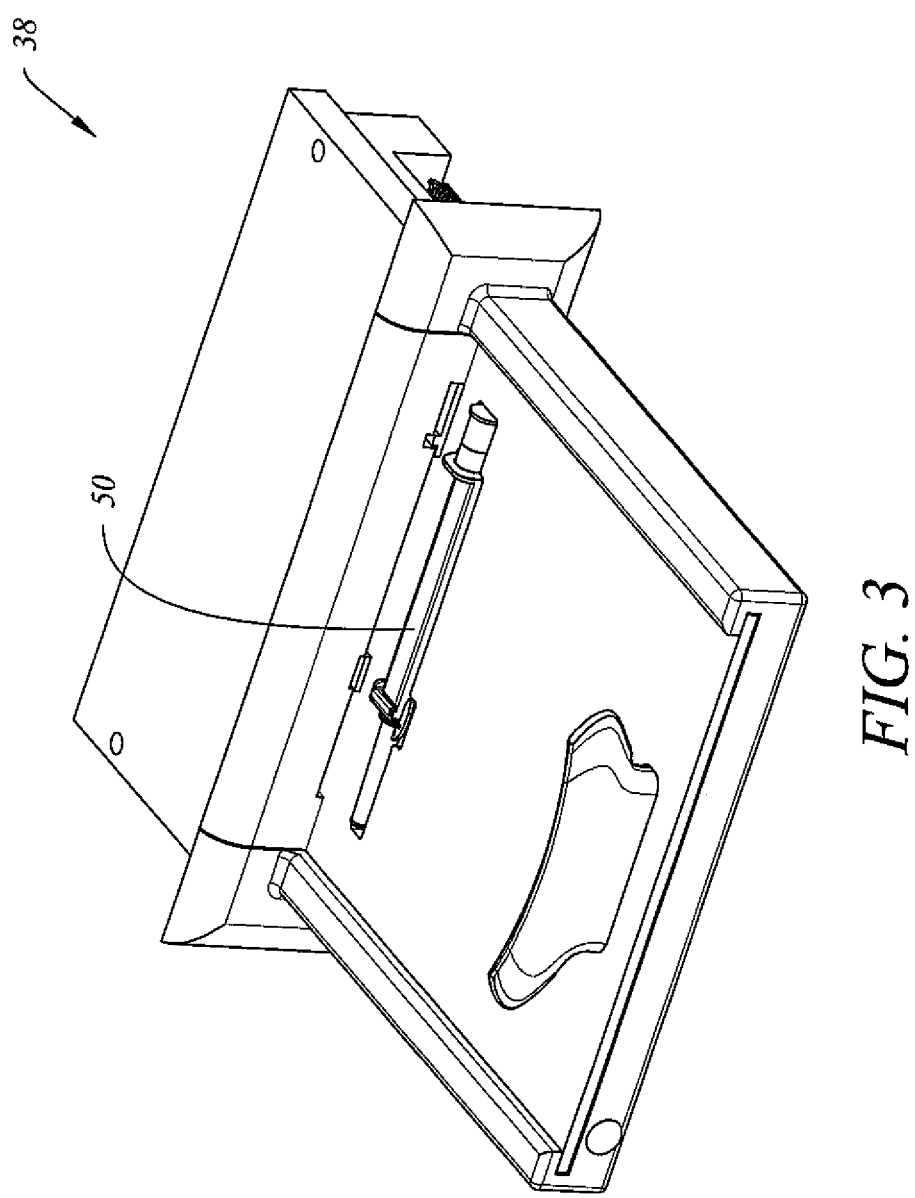
FIG. 3 is the apparatus shown in FIG. 2 with the syringe inserted into the template portion of the drawer or carriage.

Referring to FIG. 2, the syringe reading/receiving/sensing mechanism 38 further comprises a drawer or carriage 42 slidable into cabinet 32 of FIG. 1. Carriage 42 comprises a template 48 into which a used syringe 50 is insertable for deposit into device 30. Push handle 46 is provided for use in pushing the used syringe, once inserted into template 48 of carriage 42 as shown in FIG. 3, into position for discharge of the used syringe into the secured storage receptacle disposed behind lockable access door 40 below syringe reading/receiving/sensing mechanism 38.

Figure 4:
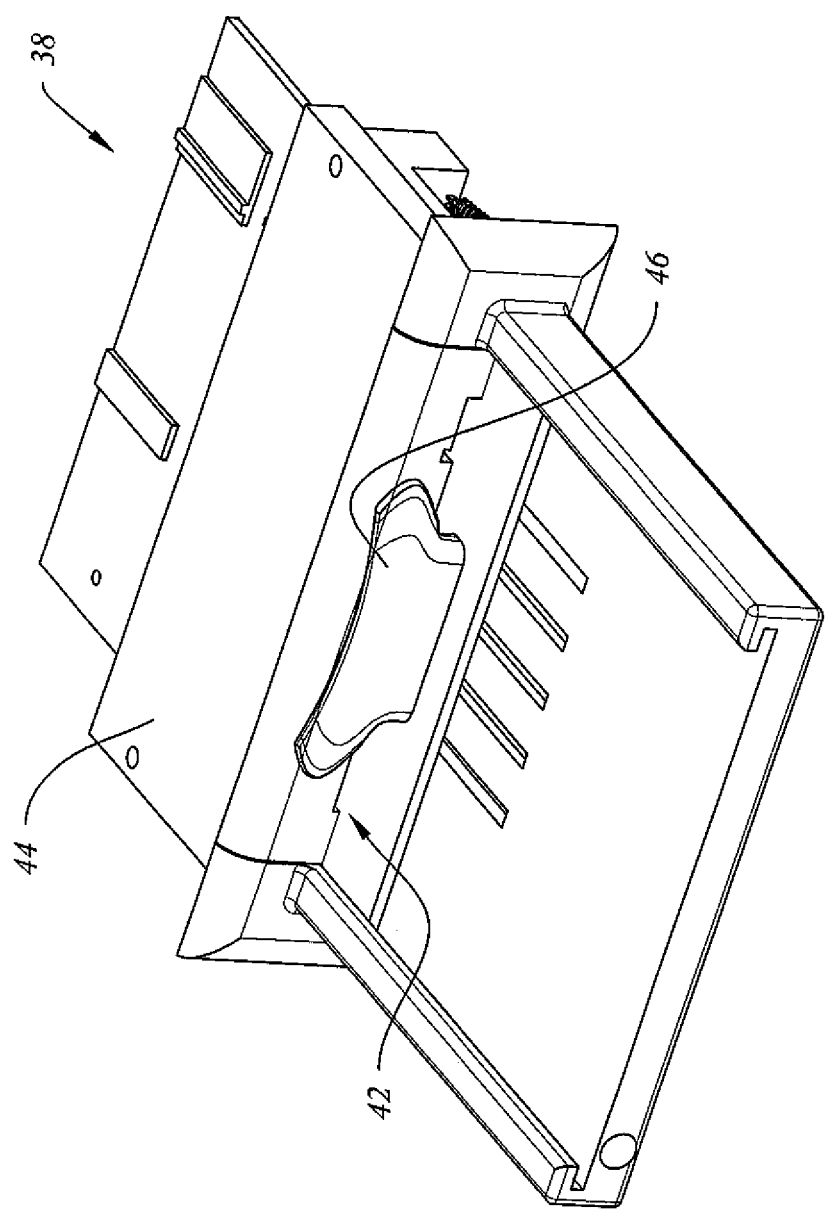
FIG. 4 is the apparatus shown in FIG. 3 with the push handle moved forwardly (as into the device) so that the syringe can be deposited into the secure storage receptacle of the device.
Figure 5:
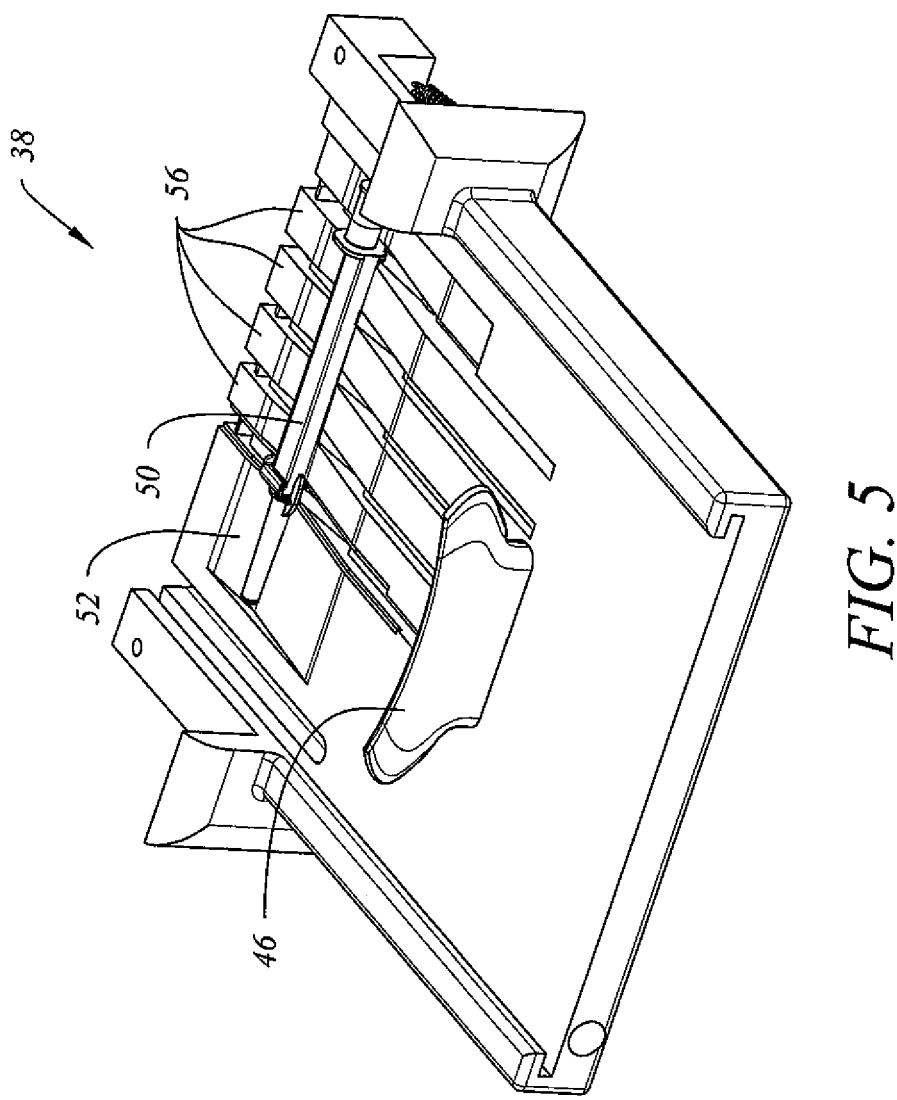
FIG. 5 is the apparatus shown in FIG. 4 with the covering structure removed to reveal a plurality of mechanical latches configured to restrict passage of apparatus not physically conforming to the template for the intended apparatus as needed for the used syringe to pass into the secure storage receptacle.

Referring to FIG. 4, push handle 46 and carriage 42 are shown moved forwardly to move the used syringe into the dispensing position. Referring to FIG. 5, cover 44 shown in FIG. 4 is removed to show the plurality of mechanical latches 56 that are configured to permit discharge of the used syringe 50 into the underlying secure storage receptacle only if syringe 50 is of the proper configuration to be passed through a plurality of restrictions imposed by the shaped latches 56.

Figure 6:
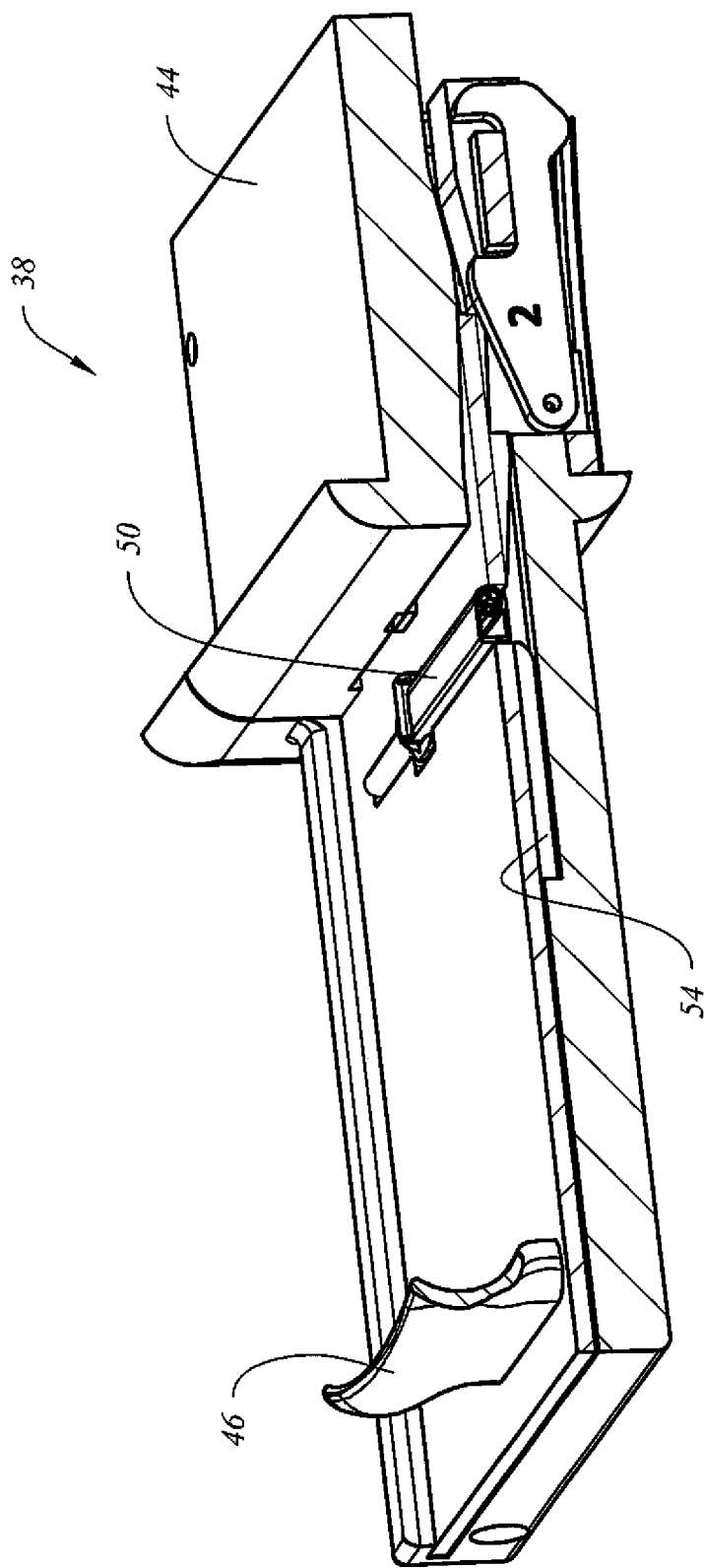
FIG. 6 is a longitudinal cross-sectional view through the reading/receiving/sensing mechanism of the device.

Referring to FIG. 6, a longitudinal cross-section through mechanism 38 is shown to depict the internal structure underlying cover 44.

It will become apparent to those of ordinary skill in the art upon reading this specification in relation to the accompanying drawings that various other modifications and alterations to the disclosed apparatus and methods can also be made, and it is intended that the scope of the invention disclosed herein be limited only by the broadest interpretation of the appended claims to which the inventors are legally entitled.

We claim:

1. A medical apparatus exchange device (30) configured to receive through a lockable access door (40) into secure storage for a previously used needle-containing medical apparatus (50) and to thereafter dispense a new, unused, sterile medical apparatus like the used apparatus, the medical apparatus exchange device (30) comprising a cabinet (32) enclosed on all sides and further comprising:
   a lockable new product loading door (34) providing access to a plurality of new, unused, sterile medical apparatus (50);
   a mechanism (38) comprising a carriage (42) slidable into cabinet (32), the carriage (42) further comprising a template 48 configured to selectively receive and deposit a previously used needle-containing medical apparatus (50) into a secure storage behind lockable access door 40; and
   a control mechanism cooperatively configured with an apparatus dispensing chute (36) to dispense one new, unused, sterile medical apparatus for each used medical apparatus deposited into secure storage.

2. The medical apparatus exchange device (30) of claim 1 wherein the slidable carriage (42) further comprises a push handle (46).

3. The medical apparatus exchange device (30) of claim 2 wherein carriage (42) further comprises a plurality of shaped mechanical latches (56).

4. The medical apparatus exchange device (30) of claim 1 wherein the new, unused, sterile medical apparatus (50) is selected from the group consisting of syringes, intravenous catheter insertion devices, bodily fluid collection devices and blood collection tube holders.

5. The medical apparatus exchange device (30) of claim 1 wherein the control mechanism comprises a touch-screen, keyboard, RFID chip or tag to identify an authorized user.

6. The medical apparatus exchange device (30) of claim 1 wherein mechanism (38) uses other parameters selected from weight, opacity or electronically recognizable indicia to authenticate and approve a used medical apparatus (50) for receipt and deposit into medical apparatus exchange device (30).

7. A medical apparatus exchange device (30) configured to receive through access door (40) into secure storage for a previously used needle-containing medical apparatus (50) and to thereafter dispense a new, unused, sterile medical apparatus like the used apparatus, the medical apparatus exchange device (30) comprising a cabinet (32) enclosed on all sides and further comprising:
   a new product loading door (34) providing access to a plurality of new, unused, sterile medical apparatus (50);
   a mechanism (38) configured to selectively receive and deposit a previously used needle-containing medical apparatus (50) into secure storage behind access door 40; and
   a control mechanism cooperatively configured with an apparatus dispensing chute (36) to dispense one new, unused, sterile medical apparatus for each used medical apparatus deposited into secure storage;
   wherein mechanism (38) comprises a carriage (42) slidable into cabinet (32); and
   wherein carriage (42) further comprises a template (48) into which a used syringe is insertable for deposit into secure storage behind access door (40) by pushing push handle (46) forwardly into cabinet (32).

8. The medical apparatus exchange device (30) of claim 7 wherein the carriage (42) further comprises a plurality of shaped mechanical latches (56).

9. The medical apparatus exchange device (30) of claim 7 wherein the new, unused, sterile medical apparatus (50) is selected from the group consisting of syringes, intravenous catheter insertion devices, bodily fluid collection devices and blood collection tube holders.

10. The medical apparatus exchange device (30) of claim 7 wherein the control mechanism comprises a touch-screen, keyboard, RFID chip or tag to identify an authorized user.

11. The medical apparatus exchange device (30) of claim 7 wherein mechanism (38) uses other parameters selected from weight, opacity or electronically recognizable indicia to authenticate and approve a used medical apparatus (50) for receipt and deposit into medical apparatus exchange device (30).

\* \* \* \* \*